ID [19]

United States Patent
Kurahashi et al.

[11] Patent Number: 5,622,914
[45] Date of Patent: Apr. 22, 1997

[54] QUINOLINE COMPOUNDS AS FUNGICIDES OR BACTERICIDES

[75] Inventors: Yoshio Kurahashi, Oyama; Koichi Moriya, Tochigi; Haruko Sawada, Ibaraki; Haruhiko Sakuma; Ryo Watanabe, both of Tochigi; Asami Ito, Tochigi, all of Japan

[73] Assignee: Nihon Bayer Agrochem K.K., Tokyo, Japan

[21] Appl. No.: 529,963

[22] Filed: Sep. 19, 1995

[30] Foreign Application Priority Data

Sep. 21, 1994 [JP] Japan .................................. 6-251620
Mar. 31, 1995 [JP] Japan .................................. 7-097670

[51] Int. Cl.$^6$ .......................... A01N 43/42; C07D 215/44
[52] U.S. Cl. .............................. 504/247; 546/162
[58] Field of Search ............................. 546/162; 504/247

[56] References Cited

U.S. PATENT DOCUMENTS 4,622,330  11/1986  Bochis et al. ........................ 514/313

FOREIGN PATENT DOCUMENTS 8606721  11/1986  WIPO .

OTHER PUBLICATIONS

Chemical Abstracts, vol. 82, No. 11, abstract No. 72873c, p. 432 (1975).
J. Elguero et al. J. Heterocyclic Chem., vol. 26, pp. 733–738 (1989).
J. Indian Chem. Soc. vol. L1, 672–673 (1974).
J. Heterocyclic Chem. 26, 733 (1989).

*Primary Examiner*—C. Warren Ivy
*Assistant Examiner*—Evelyn Huang
*Attorney, Agent, or Firm*—Sprung Horn Kramer & Woods

[57] ABSTRACT

Combatting fungi and bacteria with quinoline derivatives of the formula

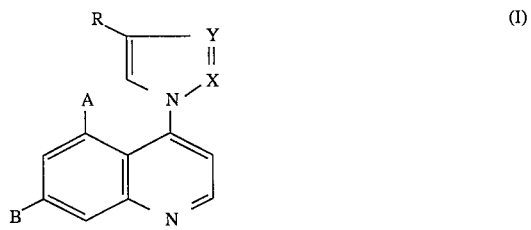

in which
X is a nitrogen atom and Y is a CH-group or
Y is a nitrogen atom and X is a CH-group,
R is hydrogen, halogen, acetyl or alkyl which is optionally substituted by one to three radicals independently selected from the group consisting of alkoxy, phenyl, hydroxy, halogen and cyano, or
R is alkenyl which is optionally substituted by one to three radicals independently selected from the group consisting of halogen, cyano, alkoxy, phenyl and hydroxy, or
R is alkynyl which is optionally substituted by one to three radicals independently selected from the group consisting of halogen, phenyl, trimethylsilyl, hydroxy, cyano, alkoxy, alkylamino, dialkylamino, alkylcarbonyl, tolyl, alkoxycarbonyl and alkylcarbonyloxy, or
R is cycloalkyl which is optionally substituted by one to three radicals independently selected from the group consisting of halogen and cyano,
A is hydrogen or halogen and
B is halogen or halogenoalkyl,
or an acid addition salt or metal salt complex thereof, and processes for their preparation. Most of these compounds are new.

9 Claims, No Drawings

QUINOLINE COMPOUNDS AS FUNGICIDES OR BACTERICIDES

The present invention relates to the use of quinoline derivatives as microbicidal agents. Further, the present invention relates to new quinoline derivatives and to processes for their preparation.

It is already known that certain quinoline derivatives have physiological activities, such as microbicidal activity or anti-protozoan activity (see J. Indian Chem. Soc. Vol. LI, 672–673 (1974) and WO 86-06 721). Further, several quinoline derivatives, such as 4-pyrazolylquinolines, have already been described as chemical compounds (see J. Heterocyclic Chem. 26, (1989) 733).

It has now been found that quinoline derivatives of the formula

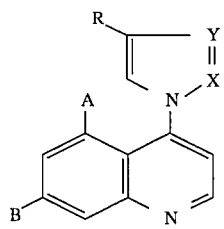

(I)

in which

X is a nitrogen atom and Y is a CH-group or
Y is a nitrogen atom and X is a CH-group,
R is hydrogen, halogen, acetyl or alkyl which is optionally substituted by one to three radicals independently selected from the group consisting of alkoxy, phenyl, hydroxy, halogen and cyano, or
R is alkenyl which is optionally substituted by one to three radicals independently selected from the group consisting of halogen, cyano, alkoxy, phenyl and hydroxy, or
R is alkynyl which is optionally substituted by one to three radicals independently selected from the group consisting of halogen, phenyl, trimethylsilyl, hydroxy, cyano, alkoxy, alkylamino, dialkylamino, alkylcarbonyl, tolyl, alkoxycarbonyl and alkylcarbonyloxy, or
R is cycloalkyl which is optionally substituted by one to three radicals independently selected from the group consisting of halogen and cyano,
A is hydrogen or halogen and
B is halogen or halogenoalkyl,
and their acid addition salts and metal salt complexes,
are outstandingly active as microbicides.

The compounds of the formula (I), in which X denotes a nitrogen atom and Y denotes a CH-group and R denotes a hydrogen atom are already known (see J. Heterocyclic Chem. 26, (1989) 733). However, microbicidal activity of such compounds has not been reported hitherto.

Thus, there have also been found novel quinoline derivatives of the formula

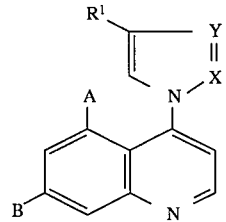

(Ia)

in which

X is a nitrogen atom and Y is a CH-group or
Y is a nitrogen atom and X is a CH-group, $R^1$ represents halogen, acetyl or alkyl, which is optionally substituted by one to three radicals selected from alkoxy, phenyl, hydroxy, halogen and cyano, or
$R^1$ represents alkenyl, which is optionally substituted by one to three radicals selected from halogen, cyano, alkoxy, phenyl and hydroxy, or
$R^1$ represents alkynyl, which is optionally substituted by one to three radicals selected from halogen, phenyl, trimethylsilyl, hydroxy, cyano, alkoxy, alkylamino, dialkylamino, alkylcarbonyl, tolyl, alkoxycarbonyl and alkylcarbonyloxy, or
$R^1$ represents cycloalkyl, which is optionally substituted by one to three radicals selected from halogen and cyano,
A is hydrogen or halogen and
B is halogen or halogenoalkyl,
and acid addition salts and metal salts complexes thereof.

After all, it has been found that quinoline derivatives of the formula (Ia) and acid addition salts and metal salt complexes thereof can be prepared by a) reacting 4-halogeno-quinolines of the formula

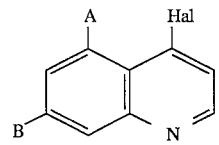

(II)

in which
A and B have the above-mentioned meanings and
Hal denotes halogen, with azoles of the formula

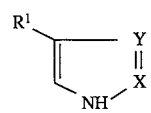

(III)

in which
$R^1$, X and Y have the above-mentioned meanings,
in the presence of an inert solvent and, if appropriate, in the presence of an acid-binder, or b) for the preparation of quinoline derivatives of the formula

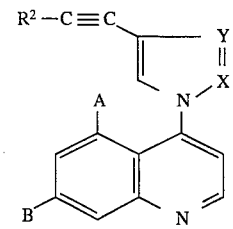

(Ib)

in which
A, B, X and Y have the above-mentioned meanings and
$R^2$ represents alkyl, which can be substituted by one to three radicals selected from halogen, phenyl, trimethylsilyl, hydroxy, cyano, alkoxy, alkylamino, dialkylamino, alkylcarbonyl, tolyl, alkoxycarbonyl and alkylcarbonyloxy, or
$R^2$ represents trimethylsilyl, reacting quinoline derivatives of the formula

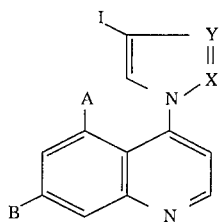

in which

A, B, X and Y have the above-mentioned meanings,
with acetylene derivatives of the formula

in which

R² has the above-mentioned meaning, in the presence of an inert solvent and, if appropriate,
in the presence of an acid binder and, if appropriate,
in the presence of a catalyst, or c) for the preparation of quinoline derivatives of the formula

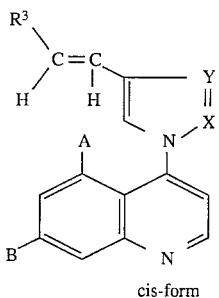

cis-form in which

A, B, X and Y have the above-mentioned meanings and
R³ represents alkyl, which is optionally substituted by one to three radicals selected from alkoxy, phenyl and hydroxy, reacting quinoline derivatives of the formula

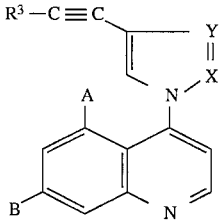

in which

A, B, R³, X and Y have the above-mentioned meanings,
with hydrogen in the presence of a catalyst and in the presence of an inert solvent, or d) for the preparation of quinoline derivatives of the formula

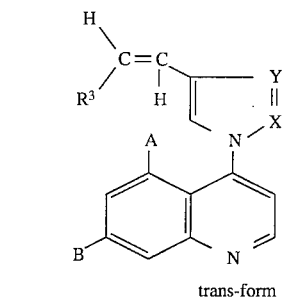

trans-form in which

A, B, R³, X and Y have the above-mentioned meanings,
heating quinoline derivatives of the formula

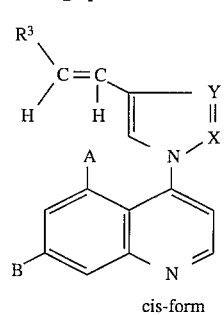

cis-form in which

A, B, R³, X and Y have the above-mentioned meanings,
in the presence of an inert solvent, or e) for the preparation of quinoline derivatives of the formula

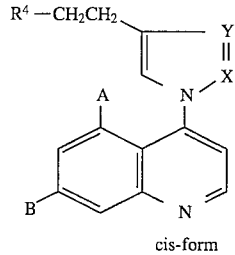

cis-form in which

R⁴ represents hydrogen or alkyl, which is optionally substituted by one to three radicals selected from alkoxy, phenyl and hydroxy, reacting quinoline derivatives of the formula

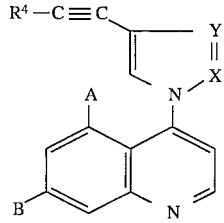

in which

A, B, R⁴, X and Y have the above-mentioned meanings,
with hydrogen in the presence of a palladium catalyst and in the presence of an inert solvent, or f) for the preparation of quinoline derivatives of the formula

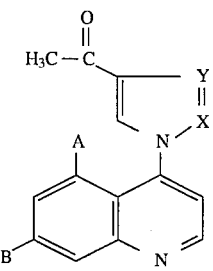

(Ih)

in which

A, B, X and Y have the above-mentioned meanings, reacting quinoline derivatives of the formula

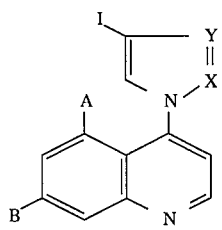

(Ic)

in which

A, B, X and Y have the above-mentioned meanings, with ethylene derivatives of the formula

$CH_2=CH-O-R^5$ (V)

in which $R^5$ denotes alkyl, in the presence of an inert solvent and, if appropriate, in the presence of a catalyst and, if appropriate, in the presence of an acid-binder, or g) for the preparation of quinoline derivatives of the formula

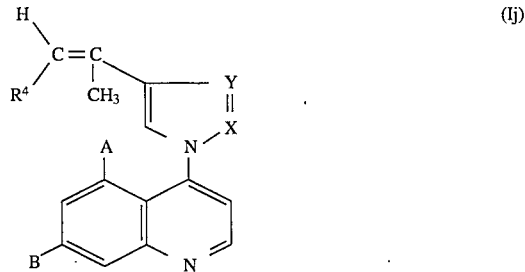

(Ij)

in which

A, B, X and Y have the above-mentioned meanings, and $R^{4'}$ represents hydrogen or alkyl, which is optionally substituted by one to three radicals selected from alkoxy and phenyl, reacting quinoline derivatives of the formula

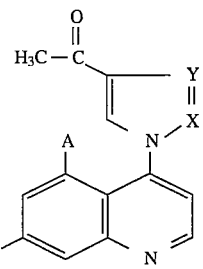

(Ih)

in which

A, B, X and Y have the above-mentioned meanigns, with phosphorus ylides of the formula

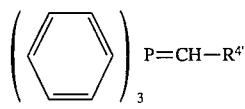

(VI)

in which $R^{4'}$ has the above-mentioned meaning in the presence of an inert solvent, and, if appropriate, adding an acid or a metal salt onto the compounds of the formula (I) thus obtained.

Surprisingly, the compounds according to the invention have a much better microbicidal activity than the already known compounds, which are structurally similar and have the same type of action.

The term "halogen" includes fluoro, chloro, bromo and iodo, and preferably represents chloro and bromo.

In the present context, "alkyl" and the alkyl part of "halogenoalkyl" can either be straight-chained or branched and include, for example, $C_1$ to $C_8$, particularly $C_1$ to C6, alkyl, such as methyl, ethyl, propyl, isopropyl, n-(iso-, sec-, tert-)butyl, n-pentyl, n-hexyl and 3,3-dimethylbutyl, and preferred among them is $C_1$ to $C_4$ alkyl, such as methyl, ethyl, propyl, isopropyl and n-(iso-, sec-, tert-)butyl.

The alkyl groups can be substituted by one to three identical or different substituents selected from halogen, cyano, alkoxy (lower alkoxy such as methoxy and ethoxy), phenyl and hydroxy. Such substituted alkyl includes, for example, bromomethyl, chloromethyl, 5-cyanopentyl, 3-methoxypropyl, phenethyl, 3-hydroxypropyl, 3-hydroxy-3-methylbutyl, etc.

In the present context, the term "alkenyl" represents straight-chain or branched alkenyl, and includes, for example, $C_2$ to $C_8$, particularly $C_2$ to $C_6$, alkenyl, such as vinyl, allyl, 1-propenyl, 1-butenyl and 3,3-dimethyl-1-butenyl, and preferred among them is $C_2$ to $C_4$ alkenyl, such as vinyl and 1-propenyl.

The alkenyl groups can be substituted by one to three, preferably by one substituent selected from halogen, cyano, alkoxy, phenyl and hydroxy. Such substituted alkenyl includes, for example, 2-cyanoethenyl, 2-chloroethenyl, styryl, 3-hydroxy1-propenyl, 3-hydroxy-3-methylbuten-1-yl, 3-methoxy-1-propenyl, etc.

In the present context, the term "alkynyl" represents straight-chain or branched alkynyl and includes, for example, $C_2$ to $C_{14}$, particularly $C_2$ to $C_{12}$, alkynyl, such as ethynyl, 1-propynyl, 1-butynyl, 1-hexynyl, 1-heptynyl, 1-octynyl, 1-nonynyl, 1-decynyl, 1-undecynyl and 1-dodecynyl, and preferred among them is $C_2$ to $C_5$ alkynyl, such as ethynyl, 1-propynyl and 1-butynyl.

The alkynyl groups can be substituted by one to three, preferably by one, substituent, selected from halogen, phenyl, trimethylsilyl, hydroxy, cyano, alkoxy (e.g., lower alkoxy, such as methoxy and ethoxy), mono- or di-alkylamino (e.g., mono- or di-(lower alkyl)amino, such as methylamino, dimethylamino, ethylamino and diethylamino), alkylcarbonyl, (e.g., lower alkylcarbonyl, such as acetyl and propionyl), tolyl, alkoxycarbonyl (e.g., lower alkoxycarbonyl, such as methoxycarbonyl and ethoxycarbonyl) and alkylcarbonyloxy (e.g., lower alkylcarbonyloxy, such as acetyloxy and propionyloxy). Specific examples of such substituted alkynyl groups are phenylethynyl, 3-hydroxy-1-propynyl, 3-hydroxy-3-methylbutyn-1-yl, 4-hydroxybutyn-1-yl, 3-chloro-1-propynyl, 5-chloropentynyl-1-yl, 3-bromo-1-propynyl, ethoxyethynyl, 3-methoxy-1-propynyl, 3-methylamino-1-propynyl, 3-dimethylamino-1-propynyl, acetylethynyl, methoxycarbonylethynyl, p-tolylethynyl, benzylethynyl, 5-cyanopentyn-1-yl, 3-acetyloxy-1-propynyl, etc.

Herein, the term "lower" means that the carbon number of a group modified with this term is 6 or less, preferably 4 or less.

In the present context, the term "cycloalkyl" preferably represents $C_3$ to $C_8$ cycloalkyl, particularly cyclopropyl.

The cycloalkyl groups can be substituted by one to three, preferably by one or two substituents selected from halogen and cyano. Specific examples of such substituted cycloalkyl are 2,2-dichlorocyclopropyl and 1-cyanocyclopropyl.

Formula (I) provides a general definition of the quinoline derivatives according to the invention. Preferred compounds of the formula (I) are those in which X is a nitrogen atom and Y is a CH-group or
Y is a nitrogen atom and X is a CH-group,
R is hydrogen, chlorine, bromine, iodine, acetyl, or straight-chain or branched alkyl having 1 to 6 carbon atoms, which alkyl groups can be substituted by one to three substituents independently selected from the group consisting of chlorine, bromine, cyano, methoxy, phenyl and hydroxy, or
R is straight-chain or branched alkenyl having 2 to 6 carbon atoms, which alkenyl groups can be substituted by one to three, preferably one, substituent selected from chlorine, bromine, cyano, methoxy, phenyl and hydroxy, or
R is straight-chain or branched alkynyl having 2 to 12 carbon atoms, which alkynyl groups can be substituted by one to three, preferably by one, substituent independently selected from the group consisting of chlorine, bromine, phenyl, trimethylsilyl, hydroxy, cyano, methoxy, ethoxy, methylamino, dimethylamino, acetyl, p-tolyl, methoxycarbonyl and acetyloxy, or
R is cycloalkyl having 3 to 6 carbon atoms, which cycloalkyl groups can be substituted by one to three, preferably one or two, substituents independently selected from the group consisting of chlorine and cyano,
A is hydrogen, fluorine, chlorine or bromine, and
B is fluorine, chlorine, bromine, iodine or trifluoromethyl.

Particularly preferred compounds of the formula (I) are those, in which

X is a nitrogen atom,
Y is a CH-group,
R is hydrogen, chlorine, bromine, iodine, acetyl or straight-chain or branched alkyl having 1 to 6 carbon atoms, which alkyl groups can be substituted by one to three substituents independently selected from the group consisting of chlorine, bromine, cyano, methoxy, phenyl and hydroxy, or
R is straight-chain or branched alkenyl having 2 to 10 carbon atoms, which alkenyl groups can be substituted by one to three, preferably one, substituent selected from chlorine, bromine, cyano, methoxy, phenyl and hydroxy, or
R is straight-chain or branched alkynyl having 2 to 10 carbon atoms, which alkynyl groups can be substituted by one to three, substituent independently selected from the group consisting of chlorine, bromine, phenyl, trimethylsilyl, hydroxy, cyano, methoxy, ethoxy, methylamino, dimethylamino, acetyl, p-tolyl, methoxycarbonyl and acetyloxy, or
R is cyclopropyl, which can be substituted by one or two substituents independently selected from the group consisting of chlorine and cyano,
A is hydrogen, chlorine or bromine and
B is fluorine, chlorine, bromine, iodine or trifluoromethyl.

Addition products of acids and those quinoline derivatives of the formula (I), in which A, B, R, X and Y have the meanings which have already been mentioned as preferred for these substituents, are also preferred compounds according to the invention.

The acids which can be added on include, preferably, hydrogen halide acids, such as, for example, hydrochloric acid and hydrobromic acid, in particular hydrochloric acid, and, furthermore, phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulphonic acid, 1,5-naphthalenedisulphonic acid or camphorsulphonic acid, as well as saccharin and thiosaccharin.

Addition products of salts of metals of main groups II to IV and of sub-groups I and II and IV or VIII of the periodic table of the elements and those quinoline derivatives of the formula (I), in which A, B, R, X and Y have the meanings which have already been mentioned as preferred for these substituents, are also preferred compounds according to the invention.

Salts of copper, zinc, manganese, magnesium, tin, iron and nickel are particularly preferred here. Possible anions of these salts are those which are derived from those acids which lead to physiologically acceptable addition products. Particularly preferred acids of this type are, in this connection, the hydrogen halide acids, such as, for example, hydrochloric acid and hydrobromic acid, and, furthermore, phosphoric acid, nitric acid and sulphuric acid.

Formula (Ia) provides a general definition of the novel quinoline derivatives according to the invention. In this formula, $R^1$ preferably has those meanings, which have already been mentioned as preferred for the substituent R. However, $R^1$ does not denote hydrogen. A, B, X and Y again preferably have those meanings which have already been mentioned as preferred for these substituents.

If 4,7-dichloroquinoline and 4-chloropyrazole are used as starting materials, the course of process (a) according to the invention can be illustrated by the following formula scheme.

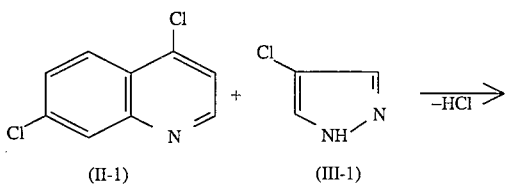

-continued

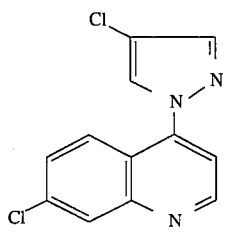

If 7-chloro-4-(4-iodo-1-pyrazolyl)-quinoline is used as starting material and trimethylsilylacetylene is used as reaction component, the course of process (b) according to the invention can be illustrated by the following formula scheme.

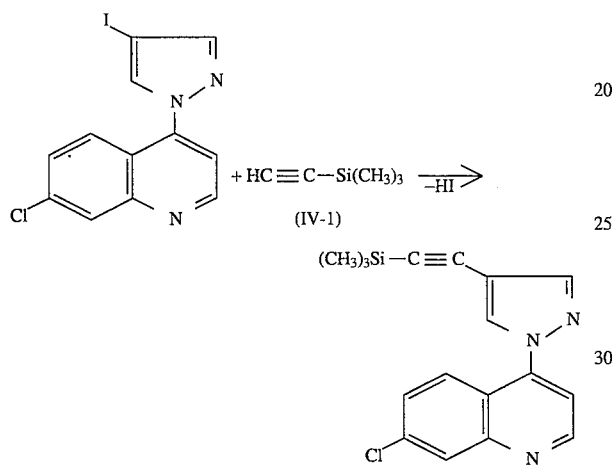

If 7-chloro-4-[4-(1-propynyl)-1-pyrazolyl]-quinoline is used as a starting material and hydrogenation is carried out with hydrogen in the presence of a Lindlar catalyst, the course of process (c) according to the invention can be illustrated by the following formula scheme.

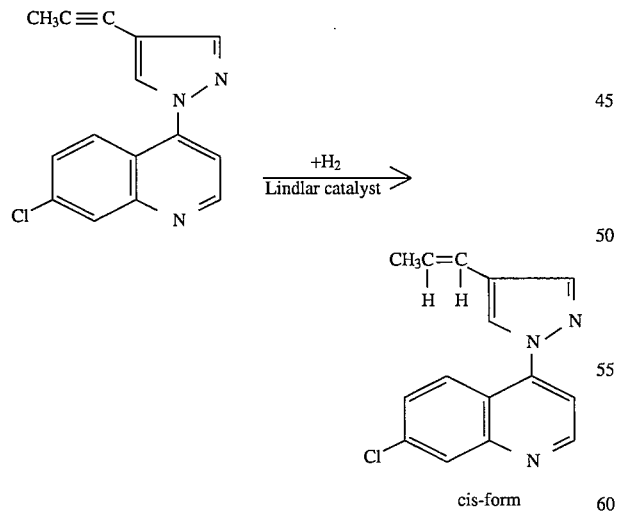

If the cis-form of 7-chloro-4-[4-(1-propenyl)-1-pyrazolyl]-quinoline is used as a starting material and is subjected to heat treatment, the course of process (d) according to the invention can be illustrated by the following formula scheme.

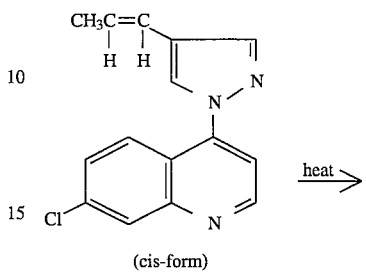

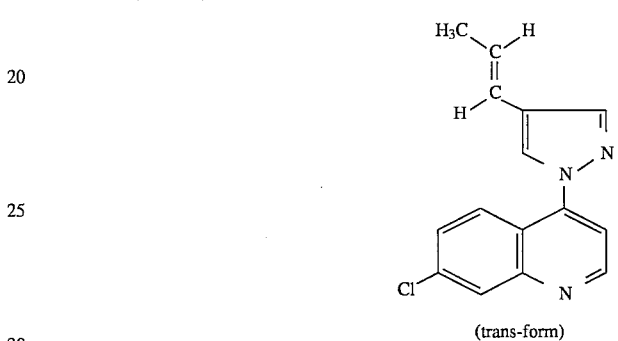

If 7-chloro-4-[4-(butyn-1-yl)-1-pyrazolyl]-quinoline is used as a starting material and hydrogenation is carried out with hydrogen in the presence of palladium-carbon catalyst, the course of process (e) according to the invention can be illustrated by the following formula scheme.

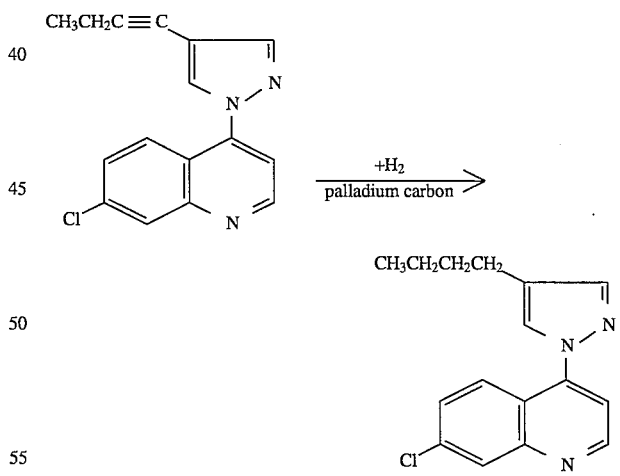

If 7-chloro-4-(4-iodo-1-pyrazolyl)-quinoline is used as a starting material and n-butyl-vinyl-ether is used as a reaction component, the course of process (f) according to the invention can be illustrated by the following formula scheme.

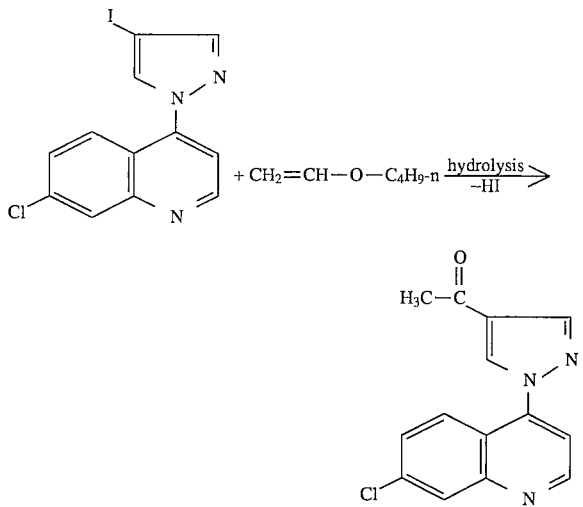

If 7-chloro-4-(4-acetyl-1-pyrazolyl)-quinoline is used as a starting material and triphenyl-methyl-phosphonium-ylide is used as a reaction component, the course of process (g) according to the invention can be illustrated by the following formula scheme.

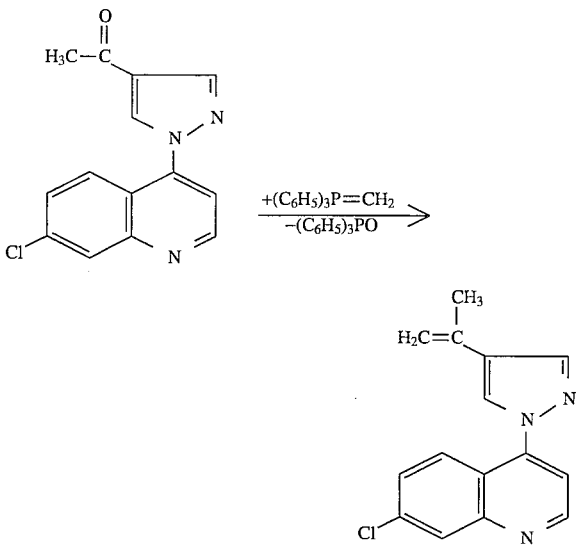

Formula (II) provides a general definition of the 4-halogeno-quinolines required as starting materials in carrying out process (a) according to the invention. In this formula, Hal preferably denotes chlorine, and A and B preferably have those meanings which have already been mentioned as preferred for these substituents in connection with the description of the compounds of the formula (I) according to the invention.

4,7-dichloro-quinoline may be mentioned as an example of the compounds of the formula (II).

The 4-halogeno-quinolines of the formula (II) are known (see J. Indian Chem. Soc. Vol. LI (1974), 672–673).

Formula (III) provides a general definition of the azoles also required as starting materials in carrying out process (a) according to the invention. In this formula $R^1$, X and Y preferably have those meanings which have already been mentioned as preferred for these substituents.

As representative examples of compounds of the formula (III), there may be mentioned 4-methyl-pyrazole, 4-chloro-pyrazole, 4-iodo-pyrazol, etc.

The azoles of the formula (III) are known or can be prepared according to known processes.

All inert organic solvents customary for such reactions can be used as diluents in carrying out process (a) according to the invention. The following can preferably be used: aliphatic, alicyclic and aromatic hydrocarbons, which may be chlorinated, such as for example, hexane, cyclohexane, petroleum ether, ligroin, benzene, toluene, xylene, methylene chloride and chlorobenzene; ethers such as, for example, diethyl ether, methyl ethyl ether, di-isopropyl ether, dibutyl ether, propylene oxide, dioxane and tetrahydrofuran; ketones such as, for example, acetone, methyl ethyl ketone, methyl isopropyl ketone and methyl isobutyl ketone; nitriles such as, for example, acetonitrile, propionitrile and acrylonitrile; alcohols such as, for example, methanol, ethanol, isopropanol, butanol and ethylene glycol; esters such as, for example, ethyl acetate and amyl acetate; acid amides such as, for example, dimethylformamide and dimethylacetamide; sulfones and sulfoxides such as, for example, dimethyl sulfoxide and sulfolane; bases such as, for example, pyridine; etc.

Suitable acid-binders for carrying out process (a) according to the invention are all customary inorganic and organic bases. Acid-binders which can preferably be used are hydroxides, carbonates, bicarbonates and alcoholates of alkali metals, tertiary amines such as, for example, triethylamine, diethylaniline, pyridine, 4-dimethyl-aminopyridine, 1,4-diazabicyclo[2,2,2]octane (DABCO) and 1,8-diazabicyclo-[5,4,0]undec-7-ene (DBU), etc.

In carrying out process (a) according to the invention, the reaction temperatures can be varied within a substantially wide range. The process is generally carried out at temperatures between about −73° C. and about +150° C., preferably between about +15° C. and about +120° C. The reaction is preferably carried out under atmospheric pressure, but, if desired, can also be carried out under elevated or reduced pressure.

When carrying out process (a) according to the invention, the ratio of the compounds of the formula (III) to the compounds of the formula (II) is not particularly limited, and can be varied over a wide range in accordance with the kinds of these compounds and reaction conditions, etc., to be used, but usually it is suitable to use the compounds of the formula (III) in the range of about 1 mol to about 1.5 mols per mol of the compounds of the formula (II).

Formula (Ic) provides a general definition of the quinoline derivatives required as starting materials in carrying out process (b) according to the invention. In this formula, A, B, X and Y preferably have those meanings, which have already been mentioned as preferred for these substituents. The compounds of the formula (Ic) can be prepared by process (a) according to the invention.

Formula (IV) provides a general definition of the acetylene derivatives required as reaction components in carrying out process (b) according to the invention. In this formula, $R^2$ preferably represents trimethylsilyl or alkyl with 1 to 10 carbon atoms, which alkyl groups can be substituted by one to three, preferably by one, substituent selected from chlorine, bromine, phenyl, trimethylsilyl, hydroxy, cyano, methoxy, ethoxy, methylamino, dimethylamino, acetyl, p-tolyl, methoxycarbonyl and acetyloxy.

Particularly preferred are compounds of the formula (IV), in which $R^2$ represents trimethylsilyl or alkyl with 1 to 8 carbon atoms, which alkyl groups can be substituted by one to three, preferably by one, substituent selected from chlorine, bromine, phenyl, trimethylsilyl, hydroxy, cyano, methoxy, ethoxy, methylamino, dimethylamino, acetyl, p-tolyl, methoxycarbonyl and acetyloxy.

As examples of compounds of the formula (IV), there may be mentioned 1-butyne, 1-pentyne, 1-hexyne, trimethylsilylacetylene, etc.

The acetylene derivatives of the formula (IV) are known or can be prepared according to known processes.

All inert organic solvents customary for such reactions can be used as diluents in carrying out process (b) according to the invention. The following can preferably be used: aromatic hydrocarbons such as, for example, benzene, toluene and xylene; ethers such as, for example, diethyl ether, methyl ethyl ether, di-isopropyl ether, dibutyl ether, propylene oxide, dioxane and tetrahydrofuran; ketones such as, for example, acetone, methyl ethyl ketone, methyl isopropyl ketone and methyl isobutyl ketone; nitriles such as, for example, acetonitrile, propionitrile and acrylonitrile; alcohols such as, for example, methanol, ethanol, isopropanol, butanol and ethylene glycol; esters such as, for example, ethyl acetate and amyl acetate; acid amides such as, for example, dimethylformamide and dimethylacetamide; bases such as, for example, pyridine and triethylamine; etc.

Suitable acid-binders for carrying out process (b) according to the invention are all customary inorganic and organic bases. Acid-binders which can preferably be used are carbonates, bicarbonates, etc., of alkali metals, tertiary amines such as, for example, triethylamine, diethylaniline, pyridine, 4-dimethylaminopyridine, 1,4diazabicyclo[2,2,2]octane (DABCO) and 1,8-diazabicyclo[5,4,0]undec-7-ene (DBU), etc. In carrying out process (b) according to the invention, the reaction temperatures can be varied within a substantially wide range. The process is generally carried out at temperatures between about −20° C. and about +150° C., preferably between about 0° C. and +120° C. The reaction is preferably carried out under atmospheric pressure, but, if desired, can also be carried out under elevated or reduced pressure.

Process (b) according to the invention is preferably carried out in the presence of a catalyst. The catalysts which can preferably be used are copper(I)iodide and di-chloro-bis-(triphenylphosphine)palladium(II).

The amount of catalyst can be varied within a certain range. If copper(I)iodide is used, it is employed in an amount of about 0.001 mol to about 0.1 mol per mol of compound of the formula (Ic). If dichloro-bis(triphenylphosphine)palladium(II) is used, it is employed in an amount of about 0.01 mol to about 0.1 mol per mol of compound of the formula (Ic).

When carrying out process (b) according to the invention, the ratio of the compounds of the formula (IV) to the compounds of the formula (Ic) is not particularly limited, and can be varied over a wide range in accordance with the kinds of these compounds and reaction conditions, etc., to be used, but usually, it is suitable to use the compounds of the formula (IV) in the range of about 1 mol to about 1.5 mols per mol of the compounds of the formula (Ic).

Formula (Ie) provides a general definition of the quinoline derivatives required as starting materials in carrying out process (c) according to the invention. In this formula, A, B, X and Y preferably have those meanings which have already been mentioned as preferred for these substituents. $R^3$ preferably represents alkyl with 1 to 4 carbon atoms, which alkyl groups can be substituted by one to three, preferably one, substituent selected from methoxy, phenyl and hydroxy.

The quinoline derivatives of the formula (Ie) can be prepared by processes (a) or (b) according to the invention.

The process (c) according to the invention is carried out in the presence of a catalyst which is suitable to be used for the reduction of an alkyne derivative to an alkene derivative. Preferred catalysts of this type are Lindlar catalysts, such as Pd—CaCO$_3$—PbO.

The amount of catalyst can be varied within a certain range. The catalyst is preferably used in an amount of about 0.001 mol to about 0.1 mol per mol of quinoline derivative of the formula (Ie).

All inert solvents customary for such reductions can be used as diluents in carrying out process (c) according to the invention. The following can preferably be used: water, aliphatic, alicyclic and aromatic hydrocarbons, which may be chlorinated, such as, for example, hexane, cyclohexane, petroleum ether, ligroin, benzene, toluene, xylene, methylene chloride and chlorobenzene; ethers such as, for example, diethyl ether, methyl ethyl ether, di-isopropyl ether, dibutyl ether, propylene oxide, dioxane and tetrahydrofuran; alcohols such as, for example, methanol, ethanol, isopropanol, butanol and ethylene glycol; esters such as, for example, ethyl acetate and amyl acetate; acid amides such as, for example, dimethylformamide and dimethylacetamide; bases such as, for example, pyridine; acids such as, for example, acetic acid; etc.

In carrying out process (c) according to the invention, the reaction temperatures can be varied within a substantially wide range. The process is generally carried out at temperatures between about −20° C. and about +150° C., preferably between about 0° C. and +120° C. The reaction is preferably carried out under atmospheric pressure, but, if desired, can also be carried out under elevated pressure.

Process (c) according to the invention is generally carried out by introducing hydrogen into the reaction mixture until the reaction is completed.

Formula (Id) provides a general definition of the quinoline derivatives required as starting materials in carrying out process (d) according to the invention. In this formula, A, B, $R^3$, X and Y preferably have those meanings which have already been mentioned as preferred for these substituents.

The quinoline derivatives of the formula (Id) can be prepared by process (c) according to the invention.

In carrying out process (d) according to the invention, the reaction temperatures can be varied within a substantially wide range. The process is generally carried out at temperatures between about 50° C. and about 250° C., preferably between about 80° C. and 170° C. The reaction is preferably carried out under atmospheric pressure, but, if desired, can also be carried out under elevated or reduced pressure.

All inert solvents customary for such isomerizations can be used as diluents in carrying out process (d) according to the invention. The following can preferably be used: water, aliphatic, alicyclic and aromatic hydrocarbons, which may be chlorinated, such as, for example, hexane, cyclohexane, petroleum ether, ligroin, benzene, toluene, xylene, methylene chloride, chloroform, carbon tetrachloride, ethylene chloride and chlorobenzene; ethers such as, for example, diethyl ether, methyl ethyl ether, di-isopropyl ether, dibutyl ether, propylene oxide, dioxane and tetrahydrofuran; ketones such as, for example, acetone, methyl ethyl ketone, methyl isopropyl ketone and methyl isobutyl ketone; nitriles such as, for example, acetonitrile, propionitrile and acrylonitrile; alcohols such as, for example, methanol, ethanol, isopropanol, butanol and ethylene glycol; esters such as, for example, ethyl acetate and amyl acetate; acid amides such as, for example, dimethylformamide and dimethylacetamide; sulfones and sulfoxides such as, for example, dimethyl sulfoxide and sulfolane; bases such as, for example, pyridine; etc.

When carrying out process (d) according to the invention, the desired amount of quinoline derivative of the formula (Id, cis-form) is heated in the presence of a solvent until the isomerization is completed.

Formula (Ig) provides a general definition of the quinoline derivatives required as starting materials in carrying out process (e) according to the invention. In this formula, A, B, X and Y preferably have those meanings, which have already been mentioned as preferred for these substituents. $R^4$ preferably represents hydrogen or alkyl with 1 to 4 carbon atoms, which alkyl groups can be substituted by one to three, preferably by one, substituent selected from methoxy, phenyl and hydroxy.

The quinoline derivatives of the formula (Ig) can be prepared by processes (a) or (b) according to the invention.

The process (e) according to the invention is carried out in the presence of a palladium catalyst, such as palladium-carbon.

The amount of catalyst can be varied within a certain range. The catalyst is preferably used in an amount of about 0.001 mol to about 0.1 mol per mol of quinoline derivative of the formula (Ig).

All inert solvents customary for such reductions can be used as diluents in carrying out process (e) according to the invention. The following can preferably be used: aliphatic, alicyclic and aromatic hydrocarbons, which may be chlorinated, such as, for example, hexane, cyclohexane, petroleum ether, ligroin, benzene, toluene, xylene, methylene chloride and chlorobenzene; ethers such as, for example, diethyl ether, methyl ethyl ether, di-isopropyl ether, dibutyl ether, propylene oxide, dioxane and tetrahydrofuran; alcohols such as, for example, methanol, ethanol, isopropanol, butanol and ethylene glycol; esters such as, for example, ethyl acetate and amyl acetate; acid amides such as, for example, dimethylformamide and dimethylacetamide; bases such as, for example, pyridine; acids such as, for example, acetic acid; etc.

In carrying out process (e) according to the invention, the reaction temperatures can be varied within a substantially wide range. The process is generally carried out at temperatures between about −20° C. and about +150° C., preferably between about 0° C. and +120° C. The reaction is preferably carried out under atmospheric pressure, but, if desired, can also be carded out under elevated pressure.

Process (e) according to the invention is generally carried out by introducing hydrogen into the reaction mixture until the reaction is completed.

Formula (V) provides a general definition of the ethylene derivatives required as reaction components in carrying out process (f) according to the invention. In this formula, $R^5$ preferably represents alkyl having 1 to 4 carbon atoms. As an example of a compound of the formula (V), there may be mentioned n-butyl vinyl ether.

The compounds of the formula (V) are known or can be prepared by known processes.

In carrying out process (f) according to the invention, all customary inert organic solvents can be used as diluents. Preferred solvents are those, which have been mentioned as preferred in connection with the description of process (b) above.

Suitable acid-binders for carrying out process (f) according to the invention are all customary inorganic and organic bases. Preferred acid-binders are those which have been mentioned as preferred in connection with the description of process (b) above.

In carrying out process (f) according to the invention, the reaction temperatures can be varied within a substantially wide range. The process is generally carried out at temperatures between about −20° C. and about +150° C., preferably between about 0° C. and +130° C. The reaction is preferably carded out under atmospheric pressure, but, if desired, can also be carried out under elevated or reduced pressure.

Process (f) according to the invention is preferably carried out in the presence of a catalyst. The catalysts which can preferably be used are palladium(II)acetate and 3-bis(diphenylphosphino)propane.

The amount of catalyst can be varied within a certain range. If palladium(II)-acetate is used, it is employed in an amount of about 0.001 mol to about 0.1 mol per mol of the compound of the formula (Ic). If 3-bis(diphenylphosphino)propane is used, it is employed in an amount of about 0.001 mol to about 0.1 mol per mol of the compound of formula (Ic).

When carrying out process (f) according to the invention, the ratio of the compounds of the formula (V) to the compounds of the formula (Ic) is not particularly limited, and can be varied over a wide range in accordance with the kinds of these compounds and reaction conditions, etc. to be used, but usually, it is suitable to use the compounds of the formula (V) in the range of about 1 mol to about 1.5 mols per mol of the compounds of the formula (Ic).

Formula (Ih) provides a general defintion of the quinoline derivatives required as starting materials in carrying out process (g) according to the invention. In this formula, A, B, X and Y preferably have those meanings which have already been mentioned as preferred for these substituents.

The quinoline derivatives of the formula (Ih) can be prepared by processes (a) or (f) according to the invention.

Formula (VI) provides a general defintion of the phosphorus ylides required as reaction components in carrying out process (g) according to the invention. In this formula, $R^4$ preferably has the meanings which have already been mentioned as preferred for this substituent.

The phosphorus ylides of the formula (VI) are known or can be prepared by known processes.

All inert organic solvents customary for such reactions can be used as diluents in carrying out process (g) according to the invention. The following can preferably be used: aliphatic, alicyclic and aromatic hydrocarbons, which may be chlorinated, such as for example, hexane, cyclohexane, petroleum ether, ligroin, benzene, toluene, xylene, methylene chloride and chlorobenzene; ethers such as, for example, diethyl ether, methyl ethyl ether, di-isopropyl ether, dibutyl ether, propylene oxide, dioxane and tetrahydrofuran; nitriles such as, for example, acetonitrile, propionitrile and acrylonitrile; acid amides such as, for example, dimethylformamide and dimethylacetamide; sulfones and sulfoxides such as, for example, dimethyl sulfoxide and sulfolane; bases such as, for example, pyridine; etc.

In carrying out process (g) according to the invention, the reaction temperatures can be varied within a substantially wide range. The process is generally carried out at temperatures between about −20° C. and about +150° C., preferably between about 0° C. and +120° C. The reaction is preferably carried out under atmospheric pressure, but, if desired, can also be carried out under elevated or reduced pressure.

When carrying out process (g) according to the invention, the ratio of the compounds of the formula (VI) to the compounds of the formula (Ih) is not particularly limited, and can be varied over a wide range in accordance with the kinds of these compounds and reaction conditions to be used, but usually it is suitable to use the compounds of the formula (VI) in the range of about 1 mol to about 1.5 mols per mol of the compounds of the formula (Ih).

The quinoline derivatives prepared according to the foregoing processes can be separated from the reaction mixtures and purified by customary methods. Purification, for instance, can be carried out by chromatography, recrystallization, etc.

The quinoline derivatives of the formula (I) can be converted into acid addition salts or metal salt complexes.

Those acids which have already been mentioned as preferred acids in connection with the description of the acid addition salts according to the invention can preferably be used to prepare acid addition salts of the compounds of formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtration, and if appropriate purified by washing with an inert organic solvent.

Those salts of metals which have already been mentioned as preferred metal salts in connection with the description of the metal salt complexes according to the invention can preferably be used to prepare metal salt complexes of the compounds of the formula (I).

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purificated by recrystallization.

The compounds according to the invention exhibit a remarkably strong microbicidal action, particularly exhibit an excellent controlling effect against various mildew fungi including *Sphaerotheca fuliginea, Erysiphe graminis*, etc.

Thus, the compounds according to the invention can be used as agricultural microbicides, such as fungicides and bactericides, for the control of undesired plant pathogens.

Generally, the compounds according to the invention can be used as fungicides against various plant diseases caused by molds belonging to Plasmodiophoromycetes, Oomycetes, Chytridiomycetes, Zygomycetes, Ascomycetes, Basidiomycetes and Deuteromycetes, and can also be used as bactericides against various plant diseases caused by bacteriae belonging to the families Pseudomonadaceae, Rhizobiaceae, Enterobacteriaceae, Corynebacteriaceae and Stroptomycetaceae.

The good toleration by plants, of the active compounds, at the concentrations required for combating plant diseases, permits treatment of above-ground parts of plants, of vegetative propagation stock and seeds, and of the soil.

The active compounds can be converted into the customary formulations, such as solutions, emulsions, wettable powders, suspensions, powders, foams, pastes, granules, tablets, aerosols, natural and synthetic materials impregnated with active compounds, very fine capsules in polymeric substances, coating compositions for use on seed, and formulations used with burning equipment, such as fumigating cartidges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents, diluents or carriers, there are suitable in the main, aromatic hydrocarbons, such as xylene, toluene or alkyl naphthalenes, chlorinated aromatic or chlorinated aliphatic hydrocarbons, such as chloro-benzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methylisobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be, used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example, iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

The preparation and use of the active compounds according to the invention can be seen from the following examples.

PREPARATION EXAMPLES

Example 1

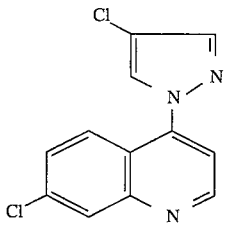

Compound No. 6

4-Chloropyrazole (1.1 g) and sodium hydride (0.5 g) were added to dimethylformamide (50 ml). The mixture was stirred at room temperature for 30 minutes, and then 4,7-dichloroquinoline (2.0 g) was added. The mixture was heated at 110° to 120° C. for 5 hours; after cooling water (150 ml) was added; and the mixture was extracted with ether (200 ml×3). The ether layers were combined and dried over anhydrous magnesium sulfate, and the solvent was distilled off under reduced pressure.

The residue was purified by silica gel column chromatography (eluent=n-hexane:ethyl acetate=7:3 v/v) to give the above-mentioned 7-chloro-4-(4-chloro-1-pyrazolyl)-quinoline (1.6 g). m.p. 110°–113.5° C.

Example 2

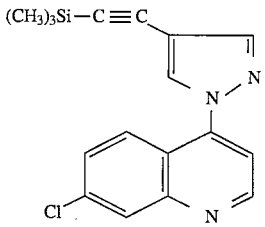

Compound No. 65

7-Chloro-4-(4-iodo-1-pyrazolyl)-quinoline (1.8 g) was dissolved in dimethylformamide (2 ml) and triethylamine (1.5 ml), copper(I)iodide (80 mg) and dichlorobis-(triphenylphosphine)palladium(II) (160 mg) were added. Then trimethylsilylacetylene (0.6 g) was added under stirring at room temperature. The mixture was stirred at room temperature for 2 hours, and the solvent was distilled off.

The residue was purified by silica gel column chromatography (eluent:chloroform) to give the above-mentioned 7-chloro-4-(4-trimethylsilylethynyl-1-pyrazolyl)-quinoline (1.4 g). m.p. 106°–112° C.

Example 3

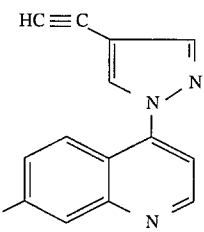

Compound No. 66

7-Chloro-4-(4-trimethylsilylethynyl-1-pyrazolyl)-quinoline (1.0 g) was dissolved in tetrahydrofuran (10 ml), and an aqueous solution (15%, 2 ml) of potassium hydroxide was added. The resulting mixture was stirred at room temperature for 5 hours.

Tetrahydrofuran was distilled off under reduced pressure, water (50 ml) was added and the mixture was extracted with dichloromethane (50 ml×3). The combined dichloromethane layers were washed with water (200 ml) and dried over anhydrous magnesium sulfate. The solvent was then distilled off under reduced pressure. The residue was purified by silica gel column chromatography (eluent:chloroform) to give the above-mentioned 7-chloro-4-(4-ethynyl-1-pyrazolyl)-quinoline (0.5 g). m.p. 174°–175° C.

Example 4

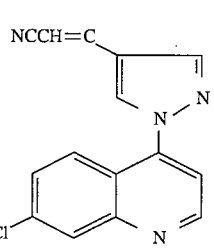

Compound No. 51 and No. 52

7-Chloro-4-(4-iodo-1-pyrazolyl)-quinoline (3.6 g) was dissolved in 1-butanol (50 ml), and then palladium(II)acetate (50 mg), acrylonitrile (5.2 g), 3-bis(diphenyl phosphino)propane (130 mg) and sodium carbonate (2.1 g) were added. The mixture was heated at 120° to 130° C. for 15 hours, and, after cooling, the precipitate was removed by suction filtration, and the solvent was distilled off.

The residue was purified by silica gel column chromatography (eluent: chloroform) to give the above-mentioned 7-chloro-4-[4-(2-cyanoethenyl)-1-pyrazolyl]-quinoline (2.6 g).
m.p.
197.5°–198.5° C. (cis-form) (Compound No. 52)
232°–239° C. (trans-form) (Compound No. 51)

Example 5

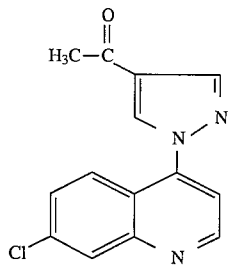

Compound No. 15

7-Chloro-4-(4-iodo-1-pyrazolyl)-quinoline (2.4 g) was dissolved in 1-butanol (150 ml), and then palladium(II)acetate (40 mg), butylvinylether (3.1 g), 3-bis(diphenylphosphino)propane (100 mg) and sodium carbonate (1.65 g) were added. The mixture was heated at 120° to 130° C. for 10 hours, and, after cooling, the solution was acidified with 6N hydrochloric acid and was stirred at room temperature for 1 hour. Ethyl acetate (200 ml) was then added and the mixture was extracted. The ethyl acetate layers were washed with water (150 ml) and dried over anhydrous magnesium sulfate. The solvent was then distilled off under reduced pressure.

The residue was purified by silica gel column chromatography (eluent: chloroform) to give the above-mentioned 7-chloro-4-(4-acetyl-1-pyrazolyl)-quinoline (1.3 g).
m.p. 190.5°–191.5° C.

Example 6

Compound No. 42

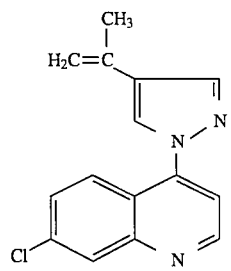

Anhydrous tetrahydrofuran (150 ml) was added to n-butyllithium (1.6M solution in hexane, 7 ml), and triphenylmethyl phosphonium bromide (3.7 g) was added under stirring at room temperature for 5 hours, and then 7-chloro-4-(4-acetyl-1-pyra-zolyl)-quinoline (2.8 g) was added. The mixture was heated at 100° to 110° C. for 10 hours, and, after cooling, the precipitate was removed by suction filtration, and the solvent was distilled off.

The residue was purified by silica gel column chromatography (eluent: chloroform) to give the above-mentioned 7-chloro-4-[4-(1-methylethenyl)-1-pyrazolyl]quinoline (0.8 g).
m.p. 85.5°–88.0° C.

Compounds obtained in the same manner as in the above examples are shown together with the compounds of the above examples in the following Tables 1 to 7. Compounds obtained according to the respective preparation processes described above are also shown therein.

TABLE 1

| Compound No. | X | Y | R | Physical Constant melting point [°C.] or refractive index [$n_D^{20}$] |
|---|---|---|---|---|
| 1 | CH | N | $CH_3$ | 143.5–146 |
| 2 | CH | N | $C_2H_5$ | |
| 3 | CH | N | $C_3H_7$-n | |
| 4 | CH | N | $C_3H_7$-iso | |
| 5 | CH | N | $C_4H_9$-iso | |
| 6 | CH | N | Cl | |
| 7 | CH | N | Br | |
| 8 | N | CH | H | 144.5–145 |
| 9 | N | CH | $CH_3$ | 116.5–117.5 |
| 10 | N | CH | $C_2H_5$ | |
| 11 | N | CH | F | |
| 12 | N | CH | Cl | 110–113.5 |
| 13 | N | CH | Br | 143.5–145.5 |
| 14 | N | CH | I | 145–147.5 |
| 15 | N | CH | $CH_3CO$ | 190.5–191.5 |
| 16 | N | CH | $C_3H_7$-n | |
| 17 | N | CH | $C_3H_7$-iso | 1.5952 |
| 18 | N | CH | $C_4H_9$-n | |
| 19 | N | CH | $C_4H_9$-sec | |
| 20 | N | CH | $C_5H_{11}$-n | |
| 21 | N | CH | $C_6H_{13}$-n | |
| 22 | N | CH | $CH_2CN$ | |
| 23 | N | CH | $CH_2CH_2CN$ | |
| 24 | N | CH | $CH_2(CH_2)_2CN$ | |
| 25 | N | CH | $CH_2(CH_2)_3CN$ | |
| 26 | N | CH | $CH_2(CH_2)_4CN$ | 78.5–81 |

TABLE 1-continued

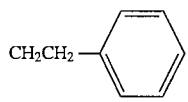

| Compound No. | X | Y | R | Physical Constant melting point [°C.] or refractive index [$n_D^{20}$] |
|---|---|---|---|---|
| 27 | N | CH | CH$_2$Br | |
| 28 | N | CH | CH$_2$(CH$_2$)$_2$Br | |
| 29 | N | CH | CCl$_3$ | |
| 30 | N | CH | CHCl$_2$ | |
| 31 | N | CH | CH$_2$(CH$_2$)$_2$Cl | |
| 32 | N | CH | CH$_2$(CH$_2$)$_4$Cl | |
| 33 | N | CH | CH$_2$(CH$_2$)$_2$OCH$_3$ | |
| 34 | N | CH |  CH$_2$CH$_2$— | |
| 35 | N | CH | CH$_2$CH$_2$C(CH$_3$)$_3$ | |
| 36 | N | CH | CH$_2$(CH$_2$)$_2$OH | |
| 37 | N | CH | CH$_2$CH$_2$C(CH$_3$)$_2$OH | |
| 38 | N | CH | 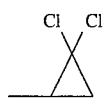 | |
| 39 | N | CH | 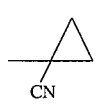 | |
| 40 | N | CH | 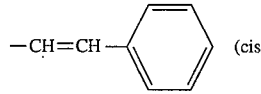 | |
| 41 | N | CH | CH=CH$_2$ | |
| 42 | N | CH | C(CH$_3$)=CH$_2$ | 85.5–88.0 |
| 43 | N | CH | —CH=CH—CH$_3$ (cis) | |
| 44 | N | CH | —CH=CH—CH$_3$ (trans) | |
| 45 | N | CH | —CH=CH—C$_2$H$_5$ (cis) | |
| 46 | N | CH | —CH=CH—C$_2$H$_5$ (trans) | |
| 47 | N | CH | —CH=CH—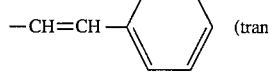 (cis) | |
| 48 | N | CH | —CH=CH—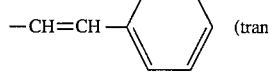 (trans) | |
| 49 | N | CH | —CH=CH—C(CH$_3$)$_3$ (cis) | |
| 50 | N | CH | —CH=CH—C(CH$_3$)$_3$ (trans) | |
| 51 | N | CH | CH=CHCN (trans) | 232–239 |
| 52 | N | CH | CH=CHCN (cis) | 197.5–198.5 |
| 53 | N | CH | CH=CHCH$_2$Cl (trans) | |
| 54 | N | CH | CH=CHCH$_2$Cl (cis) | |
| 55 | N | CH | CH=CH(CH$_2$)$_3$Cl (trans) | |
| 56 | N | CH | CH=CH(CH$_2$)$_3$Cl (cis) | |
| 57 | N | CH | CH=CHCH$_2$Br (trans) | |
| 58 | N | CH | CH=CHCH$_2$Br (cis) | |
| 59 | N | CH | —CH=CHCH$_2$OH (cis) | |
| 60 | N | CH | —CH=CHCH$_2$OH (trans) | |
| 61 | N | CH | —CH=CHC(CH$_3$)$_2$OH (cis) | |
| 62 | N | CH | —CH=CHC(CH$_3$)$_2$OH (trans) | |
| 63 | N | CH | —CH=CHCHOCH$_3$ (cis) | |
| 64 | N | CH | —CH=CHCH$_2$OCH$_3$ (trans) | |

TABLE 1-continued

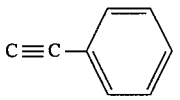

| Compound No. | X | Y | R | Physical Constant melting point [°C.] or refractive index [$n_D^{20}$] |
|---|---|---|---|---|
| 65 | N | CH | C≡C—Si(CH₃)₃ | 106–112 |
| 66 | N | CH | C≡CH | 174–175.5 |
| 67 | N | CH | C≡CCH₃ | 110.5–116.5 |
| 68 | N | CH | C≡CC₂H₅ | 83.5–85 |
| 69 | N | CH | C≡C—C₃H₇-n | 87.5–90 |
| 70 | N | CH | C≡C—C₄H₉-n | 64–72 |
| 71 | N | CH | C≡C—C₆H₅ | 138–140.5 |
| 72 | N | CH | C≡C—C(CH)₃ | 120.5–123 |
| 73 | N | CH | C≡C—CH₂OH | 179.5–182.5 |
| 74 | N | CH | C≡C—C(CH₃)₂OH | 114–118.5 |
| 75 | N | CH | C≡C—CH₂CH₂OH | |
| 76 | N | CH | C≡C—CH₂(CH₂)₃CH₃ | |
| 77 | N | CH | C≡C—CH₂(CH₂)₄CH₃ | |
| 78 | N | CH | C≡C—CH₂(CH₂)₅CH₃ | |
| 79 | N | CH | C≡C—CH₂(CH₂)₆CH₃ | |
| 80 | N | CH | C≡C—CH₂Cl | |
| 81 | N | CH | C≡C—CH₂(CH₂)₂Cl | 184–85.5 |
| 82 | N | CH | C≡C—CH₂Br | |
| 83 | N | CH | C≡COC₂H₅ | |
| 84 | N | CH | C≡C—CH₂OCH₃ | 106.5–108.5 |
| 85 | N | CH | C≡C—CH₂NHCH₃ | |
| 86 | N | CH | C≡C—CH₂N(CH₃)₂ | |
| 87 | N | CH | C≡C—C(O)—CH₃ | |
| 88 | N | CH | C≡C—COOCH₃ | 181–181.5 |
| 89 | N | CH | C≡C—C₆H₄—CH₃ | |
| 90 | N | CH | C≡C—CH₂—C₆H₅ | |

TABLE 1-continued

| Compound No. | X | Y | R | Physical Constant melting point [°C.] or refractive index [$n_D^{20}$] |
|---|---|---|---|---|
| 91 | N | CH | C≡C—CH$_2$(CH$_2$)$_2$CN | |
| 92 | N | CH | C≡C—CH$_2$O—COCH$_3$ | |
| 93 | N | CH | C≡C—C(CH$_3$)$_2$O—COCH$_3$ | |

TABLE 2

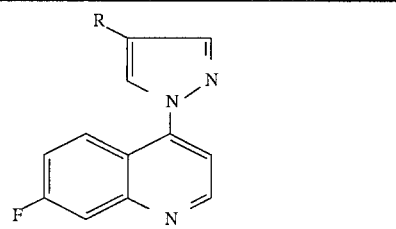

| Compound No. | R | Physical Constant melting point [°C.] or refractive index [$n_D^{20}$] |
|---|---|---|
| 94 | Cl | |
| 95 | Br | 148.5–149.5 |
| 96 | I | 133.5–136 |
| 97 | H | 143–146 |
| 98 | CH$_3$ | |
| 99 | C$_2$H$_5$ | |
| 100 | C$_3$H$_7$-n | |
| 101 | C$_3$H$_7$-iso | |
| 102 | C$_4$H$_9$-n | |
| 103 | CH$_2$CN | |
| 104 | CH$_2$CH$_2$CN | |
| 105 | CH$_2$(CH$_2$)$_4$CN | |
| 106 | CH$_2$Br | |
| 107 | CH$_2$Cl | |
| 108 | CH=CH$_2$ | |
| 109 | CH=CHCH$_3$ (cis) | |
| 110 | CH=CHCH$_3$ (trans) | |
| 111 | CH=CHCN (cis) | |
| 112 | CH=CHCN (trans) | |
| 113 | CH=CHCl (cis) | |
| 114 | CH=CHCl (trans) | |
| 115 | C≡CH | |
| 116 | C≡C—CH$_3$ | |
| 117 | ▲ | |
| 118 | ▲ with C, Cl | |

TABLE 3

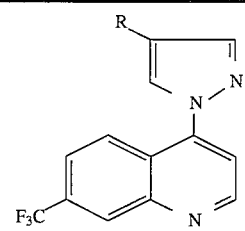

| Compound No. | R | Physical Constant melting point [°C.] or refractive index [$n_D^{20}$] |
|---|---|---|
| 119 | Cl | 52–62 |
| 120 | Br | 67–68 |
| 121 | I | 88–89 |
| 122 | H | 52.5–55 |
| 123 | CH$_3$ | 53-55.5 |
| 124 | C$_2$H$_5$ | |
| 125 | C$_3$H$_7$-n | 1.5739 |
| 126 | C$_3$H$_7$-iso | |
| 127 | C$_4$H$_9$-n | |
| 128 | CH$_2$CN | |
| 129 | CH$_2$CH$_2$CN | |
| 130 | CH$_2$(CH$_2$)$_4$CN | |
| 131 | CH$_2$Br | |
| 132 | CH$_2$Cl | |
| 133 | CH=CH$_2$ | |
| 134 | CH=CHCH$_3$ (cis) | |
| 135 | CH=CHCH$_3$ (trans) | |
| 136 | CH=CHCN (cis) | |
| 137 | CH=CHCN (trans) | |
| 138 | CH=CHCl (cis) | |
| 139 | CH=CHCl (trans) | |
| 140 | C≡CH | |
| 141 | C≡C—CH$_3$ | 115.5–118 |
| 142 | ▲ | |
| 143 | ▲ with C, Cl | |

TABLE 4

[Structure: 7-bromoquinoline with pyrazole substituent bearing R group]

| Compound No. | R | Physical Constant melting point [°C.] or refractive index [$n_D^{20}$] |
|---|---|---|
| 144 | Cl | |
| 145 | Br | 148–149.5 |
| 146 | I | 154–156.5 |
| 147 | H | |
| 148 | CH$_3$ | |
| 149 | C$_2$H$_5$ | |
| 150 | C$_3$H$_7$-n | |
| 151 | C$_3$H$_7$-iso | |
| 152 | C$_4$H$_9$-n | |
| 153 | CH$_2$CN | |
| 154 | CH$_2$CH$_2$CN | |
| 155 | CH$_2$(CH$_2$)$_4$CN | |
| 156 | CH$_2$Br | |
| 157 | CH$_2$Cl | |
| 158 | CH=CH$_2$ | |
| 159 | CH=CHCH$_3$ (cis) | |
| 160 | CH=CHCH$_3$ (trans) | |
| 161 | CH=CHCN (cis) | |
| 162 | CH=CHCN (trans) | |
| 163 | CH=CHCl (cis) | |
| 164 | CH=CHCl (trans) | |
| 165 | C≡CH | |
| 166 | C≡C—CH$_3$ | 115.5–118 |
| 167 | cyclopropyl | |
| 168 | 1-chloro-cyclopropyl-methyl | |

TABLE 5

[Structure: 5,7-dibromoquinoline with pyrazole substituent bearing R group]

| Compound No. | R | Physical Constant melting point [°C.] or refractive index [$n_D^{20}$] |
|---|---|---|
| 169 | Cl | |
| 170 | Br | |
| 171 | I | |
| 172 | H | |
| 173 | CH$_3$ | |
| 174 | C$_2$H$_5$ | |
| 175 | C$_3$H$_7$-n | |
| 176 | C$_3$H$_7$-iso | |
| 177 | C$_4$H$_9$-n | |
| 178 | CH$_2$CN | |
| 179 | CH$_2$CH$_2$CN | |
| 180 | CH$_2$(CH$_2$)$_4$CN | |
| 181 | CH$_2$Br | |
| 182 | CH$_2$Cl | |
| 183 | CH=CH$_2$ | |
| 184 | CH=CHCH$_3$ (cis) | |
| 185 | CH=CHCH$_3$ (trans) | |
| 186 | CH=CHCN (cis) | |
| 187 | CH=CHCN (trans) | |
| 188 | CH=CHCl (cis) | |
| 189 | CH=CHCl (trans) | |
| 190 | C≡CH | |
| 191 | C≡C—CH$_3$ | |
| 192 | cyclopropyl | |
| 193 | 1-chloro-cyclopropyl-methyl | |

TABLE 6

[Structure: 7-iodoquinoline with pyrazole substituent bearing R group]

| Compound No. | R | Physical Constant melting point [°C.] or refractive index [$n_D^{20}$] |
|---|---|---|
| 194 | Cl | 131–131.5 |
| 195 | Br | 131.5–133 |
| 196 | I | 164.5–166 |
| 197 | H | 146–147 |
| 198 | CH$_3$ | 119.5–120.5 |
| 199 | C$_2$H$_5$ | |
| 200 | C$_3$H$_7$-n | |
| 201 | C$_3$H$_7$-iso | |
| 202 | C$_4$H$_9$-n | |
| 203 | CH$_2$CN | |
| 204 | CH$_2$CH$_2$CN | |
| 205 | CH$_2$(CH$_2$)$_4$CN | |
| 206 | CH$_2$Br | |
| 207 | CH$_2$Cl | |
| 208 | CH=CH$_2$ | |
| 209 | CH=CHCH$_3$ (cis) | |
| 210 | CH=CHCH$_3$ (trans) | |
| 211 | CH=CHCN (cis) | |
| 212 | CH=CHCN (trans) | |
| 213 | CH=CHCl (cis) | |

TABLE 6-continued

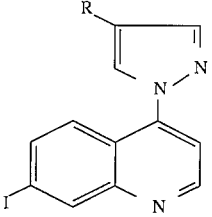

| Compound No. | R | Physical Constant melting point [°C.] or refractive index [$n_D^{20}$] |
|---|---|---|
| 214 | CH=CHCl (trans) | |
| 215 | C≡CH | |
| 216 | C≡C—CH₃ | |
| 217 |  | |
| 218 |  | |

TABLE 7

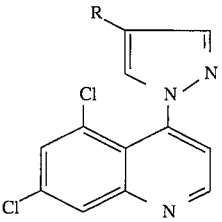

| Compound No. | R | Physical Constant melting point [°C.] or refractive index [$n_D^{20}$] |
|---|---|---|
| 219 | Cl | 135.5–136.5 |
| 220 | Br | 158.5–159.5 |
| 221 | I | 171.5–172.5 |
| 222 | H | 73–76.5 |
| 223 | CH₃ | 104.5–106 |
| 224 | C₂H₅ | |
| 225 | C₃H₇-n | |
| 226 | C₃H₇-iso | |
| 227 | C₄H₉-n | |
| 228 | CH₂CN | |
| 229 | CH₂CH₂CN | |
| 230 | CH₂(CH₂)₄CN | |
| 231 | CH₂Br | |
| 232 | CH₂Cl | |
| 233 | CH=CH₂ | |
| 234 | CH=CHCH₃ (cis) | 112–117 |
| 235 | CH=CHCH₃ (trans) | |
| 236 | CH=CHCN (cis) | |
| 237 | CH=CHCN (trans) | |
| 238 | CH=CHCl (cis) | |
| 239 | CH=CHCl (trans) | |
| 240 | C≡CH | |
| 241 | C≡C—CH₃ | 147–148.5 |
| 242 |  | |

TABLE 7-continued

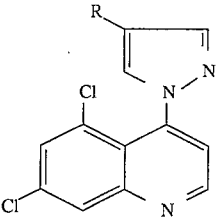

| Compound No. | R | Physical Constant melting point [°C.] or refractive index [$n_D^{20}$] |
|---|---|---|
| 243 | 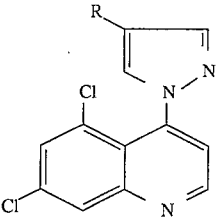 | |

USE EXAMPLES

Example 7

Cucumber—Powdery Mildew/Control Test Formulation of Active Compounds (Emulsion)

| | |
|---|---|
| Active compound | 30 parts |
| Organic solvent (xylene) | 55 parts |
| Emulsifier: | |
| polyoxyethylene alkyl phenyl ether | 8 parts |
| calcium alkylbenezenesulfonate | 7 parts |

Predetermined amounts of the emulsion are diluted with water and used for the test.

Test method

The test compound in the emulsion form was applied to two-leaf stage cucumber plants (*Sagami-hanjiro* variety) cultivated in 9 cm vinyl pots, using a spray gun. One day after the application, a spore suspension of the pathogen (*Sphaerotheca fuliginea*) was sprayed and inoculated on the cucumber plants. The pots were allowed to stand in a room at a constant temperature of 23° C. 10 days after the application, disease incidence rates were determined based on the rates of the lesion area, and control effects were calculated.

| Disease incidence rate | lesion area (%) |
|---|---|
| 0 | 0 |
| 0.5 | under 2 |
| 1 | under 2–5 |
| 2 | under 5–15 |
| 3 | under 15–30 |
| 4 | under 30–50 |
| 5 | 50 or more |

$$\text{Control effect (\%)} = \frac{\text{Disease incidence rate of untreated plot} - \text{Disease incidence rate of treated plot}}{\text{Disease incidence rate of untreated plot}} \times 100$$

The results are shown in the following Table 8.

TABLE 8

| Compound No. | Concentration of active ingredient (ppm) | Control effect (%) |
|---|---|---|
| 1 | 50 | 100 |
| 8 | 50 | 100 |
| 9 | 50 | 100 |
| 12 | 50 | 96 |
| 13 | 50 | 98 |
| 65 | 100 | 99 |
| 66 | 100 | 100 |
| 67 | 100 | 99 |
| 71 | 100 | 85 |
| 72 | 100 | 80 |
| Comparison Compound (A)* | 100 | 0 |

*known from J. Heterocyclic Chem., Vol. 26, 733 (1989).

COMPARISON COMPOUND

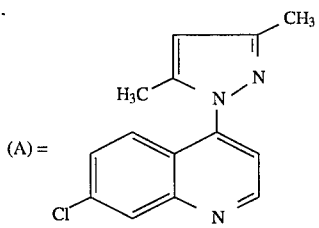

(A) =

Example 8

Barley—Powdery Mildew/Control Test Formulation of Active Compounds (Wettable Powder)

| | |
|---|---|
| Active compound | 30–40 parts by weight |
| Carrier: mixture of (1:5) of diatomaceous earth and kaolin | 55–65 parts by weight |
| Emulsifier: polyoxyethylene alkyl phenyl ether | 5 parts by weight |

The above amounts each of the active compound, the carrier and the emulsifier are ground and mixed to give a wettable powder.

Predetermined amounts thereof are diluted with water and used for the test.

Test method

About 10 grains each of barley (*Haruna-ni-jo* variety) were sown in vinyl pots each having a diameter of 7 cm, and the seedlings were grown in a greenhouse (15°–25° C.). Each wettable powder prepared in the same manner as above was diluted to predetermined concentrations, and 25 ml portions per 3 pots of each dilution were applied to the small seedlings which reached the two-leaf stage. Conidia formed on the pathogenic lesion of barley—powdery mildew previously caused by infection lesion were inoculated by scattering them on the leaves of the barley plants one day after the application (protective effect) or two days before the application (curative effect). The pots were kept in a greenhouse at 15° to 20° C. Seven days after sowing, the disease incidence rate in each pot was classificatorily evaluated according to the following criterion, and the preventive value was calculated. Each result is the average of the three pots.

| Disease incidence rate | Rate of pathogenic macula area (%) |
|---|---|
| 0 | 0 |
| 0.5 | 2 or less |
| 1 | 2–5 or less |
| 2 | 5–10 or less |
| 3 | 10–20 or less |
| 4 | 20–40 or less |
| 5 | 40–100 |

$$\text{Control effect (\%)} = \frac{\text{Disease incidence rate of untreated plot} - \text{Disease incidence rate of treated plot}}{\text{Disease incidence rate of untreated plot}} \times 100$$

TABLE 9

| Compound No. | Concentration of active ingredient (ppm) | Control effect protective (%) | curative (%) |
|---|---|---|---|
| 65 | 500 | 92 | |
| | 100 | | 100 |
| 66 | 500 | 85 | |
| | 100 | | 100 |
| 67 | 500 | 100 | |
| | 100 | | 100 |
| 68 | 500 | 80 | |
| | 100 | | 100 |
| 69 | 500 | 80 | |
| | 100 | | 100 |
| 83 | 500 | 83 | |
| | 100 | | 100 |
| Comparison Compound (A) | 500 | 0 | 0 |

Formulation Examples

Example 9

15 parts by weight of Compound No. 9 according to the invention, 80 parts by weight of a mixture (1:5) of powdery diatomaceous earth and powdery clay, 2 parts by weight of sodium alkylbenzenesulfonate and 3 parts by weight of sodium alkylnaphthalenesulfonate-formalin condensate are ground and mixed to give a wettable powder.

Example 10

15 parts by weight of Compound No. 67 according to the invention, 80 parts by weight of a mixture (1:5) of white carbon (hydrous amorphous silicon oxide fine powder) and powdery clay, 2 parts by weight of sodium alkylbenzenesulfonate and 3 parts by weight of sodium alkylnaphthalenesulfonate-formalin condensate are ground and mixed to give a wettable powder.

Example 11

30 parts by weight of Compound No. 65 according to the invention, 55 parts by weight of xylene, 8 parts by weight of polyoxyethylene alkyl phenyl ether and 7 pans by weight of calcium alkylbenzenesulfate are mixed and stirred to give an emulsion.

It will be understood that the specification and examples are illustrative but not limitative of othe present invention and that other embodiments within the spirit and scope of the invention will suggest themselves to those skilled in the art.

What is claimed is:

1. A method of using a quinoline compound of formula I as a fungicide or a bactericide which comprises applying to fungi or bacteria or to a locus from which it is desired to exclude such fungi or bacteria a fungicidally or bactericidally effective amount of quinoline compound of the formula

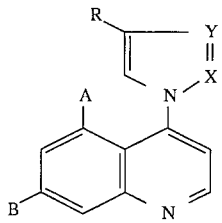

in which

X is a nitrogen atom and Y is a CH-group or
Y is a nitrogen atom and X is a CH-group,
R is hydrogen, halogen, acetyl or alkyl which is optionally substituted by one to three radicals independently selected from the group consisting of alkoxy, phenyl, hydroxy, halogen and cyano, or
R is alkenyl which is optionally substituted by one to three radicals independently selected from the group consisting of halogen, cyano, alkoxy, phenyl and hydroxy, or
R is alkynyl which is optionally substituted by one to three radicals independently selected from the group consisting of halogen, phenyl, trimethylsilyl, hydroxy, cyano, alkoxy, alkylamino, dialkylamino, alkylcarbonyl, tolyl, alkoxycarbonyl and alkylcarbonyloxy, or
R is cycloalkyl which is optionally substituted by one to three radicals independently selected from the group consisting of halogen and cyano,
A is hydrogen or halogen and
B is halogen or halogenoalkyl,
or an acid addition salt or metal salt complex thereof.

2. The method according to claim 1, wherein X is a CH-group and Y is a nitrogen atom.

3. The method according to claim 1, wherein
R is halogen, acetyl or alkyl which is optionally substituted by one to three radicals independently selected from the group consisting of alkoxy, phenyl, hydroxy, halogen and cyano, or
R is alkenyl which is optionally substituted by one to three radicals independently selected from the group consisting of halogen, cyano, alkoxy, phenyl and hydroxy, or
R is alkynyl which is optionally substituted by one to three radicals independently selected from the group consisting of halogen, phenyl, trimethylsilyl, hydroxy, cyano, alkoxy, alkylamino, dialkylamino, alkylcarbonyl, tolyl, alkoxycarbonyl and alkylcarbonyloxy, or
R is cycloalkyl which is optionally substituted by one to three radicals independently selected from the group consisting of halogen and cyano.

4. The method according to claim 1, wherein
R is hydrogen, chlorine, bromine, iodine, acetyl, or straight-chain or branched alkyl having 1 to 6 carbon atoms, which alkyl groups can be substituted by one to three substituents independently selected from the group consisting of chlorine, bromine, cyano, methoxy, phenyl and hydroxy, or
R is straight-chain or branched alkenyl having 2 to 6 carbon atoms, which alkenyl groups can be substituted by one to three, preferably one, substituent selected from chlorine, bromine, cyano, methoxy, phenyl and hydroxy, or R is straight-chain or branched alkynyl having 2 to 12 carbon atoms, which alkynyl groups can be substituted by one to three, preferably by one, substituent independently selected from the group consisting of chlorine, bromine, phenyl, trimethylsilyl, hydroxy, cyano, methoxy, ethoxy, methylamino, dimethylamino, acetyl, p-tolyl, methoxycarbonyl and acetyloxy, or
R is cycloalkyl having 3 to 6 carbon atoms, which cycloalkyl groups can be substituted by one to three, preferably one or two, substituents independently selected from the group consisting of chlorine and cyano,
A is hydrogen, fluorine, chlorine or bromine, and
B is fluorine, chlorine, bromine, iodine or trifluoromethyl.

5. The method according to claim 1, wherein
X is a nitrogen atom,
Y is a CH-group,
R is hydrogen, chlorine, bromine, iodine, acetyl or straight-chain or branched alkyl having 1 to 6 carbon atoms, which alkyl groups can be substituted by one to three substituents independently selected from the group consisting of chlorine, bromine, cyano, methoxy, phenyl and hydroxy, or
R is straight-chain or branched alkynyl having 2 to 10 carbon atoms, which alkynyl groups can be substituted by one to three, substituent independently selected from the group consisting of chlorine, bromine, phenyl, trimethylsilyl, hydroxy, cyano, methoxy, ethoxy, methylamino, dimethylamino, acetyl, p-tolyl, methoxycarbonyl and acetyloxy, or
R is cyclopropyl, which can be substituted by one or two substituents independently selected from the group consisting of chlorine and cyano,
A is hydrogen, chlorine or bromine and
B is fluorine, chlorine, bromine, iodine or trifluoromethyl.

6. The method according to claim 1, wherein the compound applied is 7-chloro-4-(4-trimethylsilylethynyl-1-pyrazolyl)-quinoline of the formula

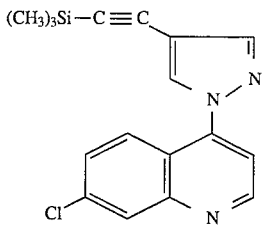

or an acid addition salt or metal salt complex thereof.

7. The method according to claim 1, wherein the compound applied is 7-chloro-4-(4-ethynyl-1-pyrazolyl)-quinoline of the formula

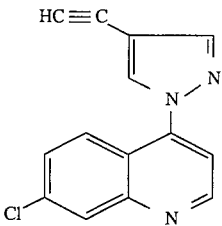

or an acid addition salt or metal salt thereof.

8. The method according to claim 1, wherein the compound applied is 7-chloro-4-(4-propynyl-1-pyrazolyl)-pyridine of the formula

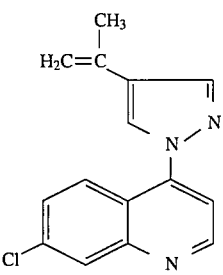

or an acid addition salt or metal salt thereof.

9. A quinoline compound of the formula

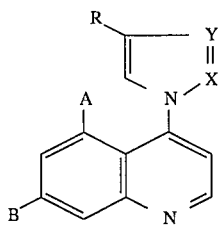

(I)

X is N

Y is CH

R is halogen, acetyl or alkyl which is optionally substituted by one to three radicals independently selected from the group consisting of alkoxy, phenyl, hydroxy, halogen and cyano, or R is alkenyl which is optionally substituted by one to three radicals independently selected from the group consisting of halogen, cyano, alkoxy, phenyl and hydroxy, or R is alkynyl which is optionally substituted by one to three radicals independently selected from the group consisting of halogen, phenyl, trimethylsilyl, hydroxy, cyano, alkoxy, alkylamino, dialkylamino, alkylcarbonyl, tolyl, alkoxycarbonyl and alkylcarbonyloxy, or R is cycloalkyl which is optionally substituted by one to three radicals independently selected from the group consisting of halogen and cyano, A is hydrogen or halogen and B is halogen or halogenoalkyl, or an acid addition salt or metal salt complex thereof.

* * * * *